(12) United States Patent
Battiste

(10) Patent No.: US 7,754,932 B2
(45) Date of Patent: **\*Jul. 13, 2010**

(54) MONITORING AND CONTROL OF PROCESSES FOR MAKING 1-HEXENE

(75) Inventor: David R. Battiste, Bartlesville, OK (US)

(73) Assignee: Chevron Phillips Chemical Company LP

( \* ) Notice: Subject to any disclaimer, the term of this patent is extended or adjusted under 35 U.S.C. 154(b) by 86 days.

This patent is subject to a terminal disclaimer.

(21) Appl. No.: 12/217,564

(22) Filed: Jul. 7, 2008

(65) Prior Publication Data

US 2008/0275282 A1    Nov. 6, 2008

Related U.S. Application Data

(63) Continuation of application No. 09/705,316, filed on Nov. 3, 2000, now Pat. No. 7,396,970.

(51) Int. Cl.
*C07C 5/00* (2006.01)
*C07C 5/08* (2006.01)

(52) U.S. Cl. .................. 585/501; 585/510; 585/520

(58) Field of Classification Search ................. 585/501, 585/510, 520
See application file for complete search history.

(56) References Cited

U.S. PATENT DOCUMENTS

| | | | |
|---|---|---|---|
| 3,682,823 A | 8/1972 | Pinole et al. | |
| 5,638,172 A | 6/1997 | Alsmeyer et al. | |
| 5,652,653 A | 7/1997 | Alsmeyer et al. | |
| 5,689,028 A | 11/1997 | Lashier et al. | |
| 5,750,817 A | 5/1998 | Tanaka et al. | |
| 6,115,528 A | 9/2000 | Schmucker et al. | |
| 6,479,597 B1 | 11/2002 | Long et al. | |

OTHER PUBLICATIONS

Clarke, Richard H. et al., Low-Resolution Raman Spectroscopy, Spectroscopy, Oct. 1998, pp. 29-35, vol. 13 (10).
Lam, Tony, A New Era in Affordable Raman Spectroscopy, Raman Technology For Today's Spectroscopies, pp. 30-37, Jun. 2004.

*Primary Examiner*—Thuan Dinh Dang
(74) *Attorney, Agent, or Firm*—Stephen R. Jenkins

(57) ABSTRACT

Processes, methods and apparatus relating to olefin oligomerization include the use of Raman spectrometry to monitor the concentration of reactants, products or other chemical components. One or more oligomerization conditions are adjusted in response to those monitored concentrations. The present processes, methods and apparatus are capable of monitoring olefin oligomerization with the use of low resolution Raman spectrometry equipment, even where there is some degree of overlap between Raman spectral peaks. Apparatus for olefin oligomerization reactions have at least one Raman probe located in the oligomerization equipment, the Raman probe providing an output signal, and Raman spectrometry equipment located outside the oligomerization equipment and operatively connected to at least one Raman probe.

13 Claims, No Drawings

MONITORING AND CONTROL OF PROCESSES FOR MAKING 1-HEXENE

CROSS-REFERENCE TO RELATED APPLICATIONS

This application claims the benefit under 35 U.S.C. §120 of U.S. application Ser. No. 09/705,316 filed on Nov. 3, 2000, which is included herein by reference in its entirety.

TECHNICAL FIELD

This invention relates to the use of Raman spectrometry in processes for the oligomerization of olefin monomers and in methods of monitoring and controlling processes for oligomerizating olefin monomers. More particularly, a Raman fiber optic probe may be placed in an ethylene-to-hexene trimerization reactor, or before or after such a reactor, for Raman spectrometric analysis. The present processes and apparatus may employ low resolution Raman spectrometry and measurement of liquid phase and/or gas phase components of an olefin oligomerization process. The present processes and apparatus allow for quantitatively monitoring a hexane preparation process in situ and constitute an improvement over gas chromatographic analysis conventionally employed in monitoring ethylene-to-hexene trimerization reactions.

BACKGROUND

Olefin monomers may be oligomerized to form oligomers. For present purposes, oligomer is defined as a series of at least two monomer units and at most roughly 300 monomer units (roughly 600 carbon atoms), and which is a liquid or waxy material at room temperature. Ethylene can be trimerized to form 1-hexene. Processes for oligomerizing olefin monomers typically employ catalyst systems comprising one or more catalytic metal compounds, typically transition metals, perhaps together with a co-catalyst and/or a support such as alumina or silica. Oligomerization processes are generally homogeneous processes. Processes for making 1-hexene from ethylene are typically homogeneous processes, in that the reactants and products are soluble in a diluent, such as isobutane.

It is desired to monitor and control the oligomerization reaction so that one may operate the process efficiently. Control of the concentration of monomer, and if present, comonomer and hydrogen, is required to ensure an efficient, reliable production process. Therefore, it is desirable to monitor the oligomerization process by determining monomer content and, when one or more co-monomers are present, by determining co-monomer content(s). It may also be desirable to determine diluent content and product content.

Current methods of monitoring oligomerization processes and the components in such processes (reactants, products and diluent) are less than optimal for several reasons. In processes for producing 1-hexene from ethylene, the contents of ethylene monomer, 1-hexene product, and by-products such as octene and decene, have typically been determined by gas chromatographic analysis of the flash gas, that is, the gas released at one of the flash tanks where pressure is released.

However, monitoring of an oligomerization process by analysis of the flash gas is less than optimal for several reasons. One reason is the amount of time for such analysis. If an analysis takes too much time, it generally has less value for monitoring, controlling or adjusting the olefin oligomerization process. Also, another concern arises when the oligomerization equipment includes more than one flash chamber, such as a high pressure flash chamber and a low pressure flash chamber. In such instances, gas chromatographic analysis of flash gas takes more time and is potentially less accurate when both high pressure and low pressure flash tanks are in operation.

While the contents of the oligomerization reactor may be determined by removing a small sample for analytical testing in a remote laboratory, this is less favorable than monitoring in situ. It may be dangerous and difficult to remove a sample from a hot process stream, and there are risks that the sample may not be representative of the overall reactor contents or that removing the sample may alter the sample. Sampling is time-consuming, and delay may cause the sample not to be representative of the reactor contents. A significant amount of material may be produced in the time required to remove, prepare, and analyze a sample. The analytical data obtained from the delayed sample is therefore of limited value for proactive process control. Furthermore, additional processing of the extracted sample may be required yet is undesirable.

A preferred method of monitoring a process for oligomerization, such as for making 1-hexene from ethylene, would monitor the process as it happens, or as soon thereafter as practical. It is also preferable that an analysis method be performed in situ, as opposed to being performed on samples removed from the oligomerization equipment. An in situ method would reduce the need to remove samples from the production environment, improve safety, and yield faster measurements. However, there are obstacles to providing in situ on-line chemical information in a process environment. The analytical method must be sufficiently accurate and precise under hostile physical and chemical conditions. The analytical method must be capable of remote detection and analysis.

Analyses of oligomerization processes in situ, that is, within a reactor or associated equipment, have been difficult if not impossible to do, since such processes are carried out at high pressures. However, spectrophotometric apparatus such as a spectrograph and a radiation source can be situated in a location remote from the reactor that is to be analyzed in situ, the sampling site being connected to the apparatus by radiation conduits comprising fiber optic cables.

Raman spectrometry can provide qualitative and quantitative information about the composition and/or molecular structure of chemical components. Raman spectrometry is based upon the vibrational energy of a compound. A sample is irradiated, preferably by a monochromatic light source, and the scattered radiation is examined through a spectrometer using photoelectric detection. Most of the scattered radiation has the wavelength of the source radiation, which is referred to as Rayleigh scattering. However, the scattered radiation also comprises radiation at shifted wavelengths, which is referred to as Raman scattering, which occur at different wavelengths due to molecular vibrations. The difference in wavelengths between the source radiation and radiation affected by molecular vibrations is commonly referred to as the Raman shift. Even if monochromatic light is used as the source radiation, the Raman spectrum will comprise scattered light spread across a wavelength band. The Raman shift or Raman spectrum conveys compositional and molecular information regarding the component in the sample. The Raman spectrum is extremely weak compared to the Rayleigh spectrum.

Not all substances are measurable by Raman spectrometry. There must be a change in polarizability during molecular vibration of a substance in order for that substance to be Raman active.

There are several factors that have favored the use of gas chromatography as an analytical method over Raman spectrometry with oligomerization processes. In general, the reactants and products in oligomerization processes may have peaks in their respective Raman spectra that are relatively close together. For example, in the trimerization of ethylene to produce hexene, the reactant ethylene and the product hexene will each produce similar peaks in their Raman spectra. Ethylene exhibits a peak at 1620 $cm^{-1}$ while hexene exhibits a peak at 1640 $cm^{-1}$. As a result, it may be difficult to distinguish between ethylene and hexene, and there is likely to be some overlap in certain peaks. Thus, it would appear necessary to employ high resolution Raman spectrometry equipment to analyze the components of the hexene preparation process. Furthermore, Raman spectrometry equipment, particularly high resolution Raman spectrometry equipment, is relatively expensive, which would generally discourage its use with industrial processes. Gas chromatography equipment has historically been less costly than high resolution Raman spectrometry equipment. Furthermore, gas chromatography sampling systems are well established. Also, gas chromatography equipment tends to provide information that is more readily usable, whereas Raman spectrometry equipment tends to produce information that requires additional analysis. Engineers and operators tend to prefer equipment that provides a relatively simple reading rather than a spectrum.

International Application No. PCT/AU86/00076, which is incorporated herein by reference, discloses monitoring the presence or concentration of one or more chemical components by using Raman scattering. Optical fibers are used to direct electromagnetic radiation to and from the monitored environment, so that the Raman detector may be remote from the monitored environment. It is stated that the Raman monitoring method is applicable to gases, liquids and solids, though no particular chemical components are disclosed as being monitored. It is also stated that it is necessary to examine the intensity of the scattered light at selected characteristic wavelengths. A band pass filter system is used, which has a series of narrow band pass interference filters each having a band pass between 100 $cm^{-1}$ and 400 $cm^{-1}$. Each filter is chosen to give maximum transmission of the Raman scattering of a particular component to be analyzed. This international application does not disclose the use of Raman spectrometry to monitor an olefin oligomerization process, or to measure olefin monomers. The international application does not disclose a method of monitoring the presence or concentration of more than one chemical component when those components have overlapping Raman spectra.

U.S. Pat. No. 5,652,653, which is incorporated herein by reference, discloses a method of on-line quantitative analysis of chemical compositions by Raman spectrometry. The method comprises simultaneously irradiating the monitored chemical composition and a reference material. The method applies predetermined calibration means to the standard Raman spectrum of the analyzed chemical composition to ascertain the chemical composition. The method is used for analyzing a polyester manufacturing process. A polyester manufacturing process generally has a liquid reaction mixture that does not include solids or a slurry. The patent discloses the construction of constitution-intensity correlation (CIC) multivariate calibration means. This is done by comparing a plurality of peaks at different wavelengths in the Raman spectra, which are preferably standard spectra, with a plurality of chemical compositions of known concentrations. The wavelengths selected for construction of a CIC depend on the spectral characteristics of the particular component whose concentration in a chemical composition is to be determined. For each component whose in situ concentration in the composition is desired to be monitored at any given time, a separate CIC calibration is prepared.

U.S. Pat. No. 4,620,284, which is incorporated herein by reference, relates to qualitative and quantitative analysis using Raman scattering for substances in gaseous, liquid and solid form to provide numbers, rather than spectra, denoting the amounts of the substances present. It is disclosed that reference spectra are used to establish a relationship between spectra region areas and concentrations of substances, and that composite reference spectra may be prepared. The patent discloses a hydrocarbon analyzer dedicated to "PNA" analysis as a particular embodiment, which determines the composition of a hydrocarbon in terms of three groups: paraffins, napthlanes, and aromatics. Among the prior art disclosed in that patent is work accomplished using the Raman effect to analyze hydrocarbons, including an article entitled "Determination of Total Olefins and Total Aromatics." Similarly, an article entitled "Low-Resolution Raman Spectroscopy," Spectroscopy 13(10) October 1998, discloses Raman spectrometric analysis of mixtures of organic liquids as well as petroleum products.

However, it is believed that Raman spectrometry has not been previously employed to monitor an olefin oligomerization process.

SUMMARY OF THE INVENTION

The present processes, methods and apparatus differ from prior processes and apparatus for monitoring chemical components with Raman spectrometry in that the present processes, methods, and apparatus are applied to processes for oligomerization, such as for preparing hexene from ethylene. Monitoring of hexene preparation processes by Raman spectrometry is distinguishable at least because the Raman spectra of the various components such as reactant and product may overlap, and other factors have made other analytical methods appear to be superior.

As one aspect, a process for olefin oligomerization is provided. The process comprises the steps of (a) providing a reaction mixture in a reactor, where the reaction mixture comprises (i) at least one reactant comprising at least one olefin monomer and optionally at least one comonomer and optionally hydrogen and (ii) a catalyst system suitable for the oligomerization of olefin monomers; (b) contacting the olefin monomer and the catalyst system in a reaction zone; (c) making an oligomer; and (d) monitoring the process by using Raman spectrometry equipment to provide an output signal representative of one or more of the reactants or the oligomer. The output signal preferably is representative of a concentration of one of the reactants or the oligomer. The olefin oligomerization may further comprise the step of adjusting the olefin oligomerization process in response to the output signal provided by the Raman spectrometry equipment, such as by adjusting the amount within the reaction mixture of at least one of the reactants or the oligomer or the catalyst system. The Raman spectrometry equipment may comprise a Raman fiber optic probe that is in contact with the reaction mixture or the polyolefin. In the present processes, the reactants may comprise hydrogen, the monomer is preferably ethylene, and the oligomer is preferably 1-hexene.

As another aspect, a method for monitoring and controlling an oligomerization process is provided. The method comprises (a) contacting in a reaction zone under suitable conditions a reaction mixture comprising monomer and a catalyst system; (b) forming an oligomer; (c) making a first measurement of a concentration of the monomer using Raman spectrometric equipment; and (d) adjusting at least one oligomerization condition in response to first measurement. The first measurement may be obtained before or within the reaction zone. In that case, the method may include making a second measurement of a concentration of the monomer using Raman spectrometric equipment, preferably within or after the reaction zone, and comparing the first concentration with the second concentration. Then, at least one oligomerization condition may be adjusted in response to the comparison. Alternatively, the first measurement may be obtained from the reaction zone in both gas phase and liquid phase using Raman spectrometric equipment.

The step of making the first measurement may comprise obtaining a Raman spectrum of the reaction mixture, and determining the first measurement through the use of a calibration model. In such cases, the calibration model should be developed prior to step (a), preferably using partial least squares analysis.

As yet another aspect, an apparatus for olefin oligomerization is provided. The apparatus comprises oligomerization equipment comprising an oligomerization reactor for oligomerizing one or more olefins; at least one inlet to the reactor for providing reactants, diluent, a catalyst system of the oligomerization; at least one outlet from the reactor for removing product from the oligomerization reactor; at least one Raman probe located in the oligomerization equipment, the Raman probe providing an output signal; Raman spectrometry equipment located outside the oligomerization equipment and operatively connected to at least one Raman probe.

The olefin oligomerization apparatus preferably also comprises a computer that receives a signal from Raman spectrometry equipment. The computer is preferably operatively connected to flow control equipment for adjusting a concentration of at least one of the reactants or the product. Alternatively, the computer is operatively connected to equipment for adjusting one or more oligomerization conditions selected from the group consisting of oligomerization temperature, oligomerization pressure, withdrawal of the reaction mixture from the reactor, and circulation rate of the reaction mixture within the reactor. The computer preferably comprises a calibration model for converting Raman spectra to at least one concentration of one or more of the reactants and product.

The Raman probe is preferably a Raman fiber optic probe disposed in the reactor or the outlet and operatively connected to the Raman spectrometry equipment by fiber optic cable.

BRIEF DESCRIPTION OF THE DRAWINGS

Not applicable.

DETAILED DESCRIPTION OF DRAWINGS AND PREFERRED EMBODIMENTS

The preferred embodiments are described in the terms of the preparation of hexene from ethylene. However, the present processes and apparatus may be employed with any oligomerization process or any process where it is desired to monitor and control the concentration of olefin monomer.

A process for preparing an oligomer such as 1-hexene is provided wherein ethylene is the monomer and 1-hexene is the product. This is a trimerization process. These and other chemical components may be monitored before, during and/or after the oligomerization reaction through Raman spectrometry. Raman spectrometry provides for improved monitoring and control of the oligomerization process. In preferred embodiments, a Raman fiber optic probe is located in the reactor and provides an output signal from which monomer and/or product and/or diluent concentrations may be determined. The present processes, methods and apparatus provide improved process control compared to process control based on flash gas analysis by gas chromatography and provide reactor operations engineers with a reliable, durable and simple way of monitoring a hexene preparation process. The species of interest in the 1-hexene process may be determined using low cost Raman spectrometry equipment. In the case of the 1-hexene process, the species of interest are ethylene, 1-hexene, solvent and decene. These compounds are reactant, primary product, solvent, and side reaction product, respectively. Octene may also be a side reaction product.

In the conversion of ethylene to 1-hexene, the reaction mixture is a homogenous clear liquid, so the Raman probe may be used in the reactor without the negative effects observed from a sample containing solid particles, such as a significant reduction in scattered radiation observed by the Raman probe. In the 1-hexene process, as well as other processes involving clear liquids, the Raman probe may be optimally placed in the reactor or in a sampling line.

Raman spectrometry typically comprises providing a source of electromagnetic radiation, transmitting the source radiation to a sample, collecting scattered radiation from the sample, separating or dispersing the energy of the scattered radiation, and detecting the scattered radiation. Any suitable radiation source may be employed in the present method and apparatus. Preferably, the radiation source provides radiation having a nominal wavelength of 785 nm, alternatively a radiation source having a nominal wavelength of 532 nm.

Suitable Raman analytical units include the low resolution Raman R-2000 and R-2001C, manufactured and marketed jointly by Ocean Optics, Inc. (Dunedin, Fla.) and Boston Advanced Technologies, Inc. (Marlboro, Mass.). Such low cost, low resolution Raman spectrometers have been found to be suitable for use in the present processes, methods and apparatus. The device consists of a solid-state diode laser with a thermoelectrically cooled charge-coupled device (CCD) array miniature detector in the R-2001C and a computer interface card. Various other and related apparatus for Raman spectrometry, as well as underlying principles, are disclosed in U.S. Pat. No. 5,652,653, which is incorporated herein by reference.

The laser in the R-2001C is a B&W diode laser set at 785 nm with a power of 500 mW. The fiber-optic probe has excitation and collection fibers that use filtering to remove most of the laser line signal from collection. The R-2001 detector is a high-sensitivity 2048-element linear CCD-array configured to detect a range of signals from 200 to 2800 cm$^{-1}$ and has a grating density of 1200 lines per mm. The detector is thermoelectrically cooled to a constant temperature of 7° C. The cooling allows for a better signal, and the constant temperature prevents having to retake dark currents to avoid floating baselines, making it ideal for longer data collection periods. The R-2001 host software that comes with the spectrometer makes the data available to the user. Spectral resolution for such a spectrometer is about 15 cm$^{-1}$, which places it in the category of low resolution Raman spectrometry equipment.

Preferably, a Raman fiber optic probe is employed in the present processes, methods, and apparatus. One suitable probe is the InPhotonics RP-785-01-05-SMA probe. The InPhotonics probe is preferred for analysis where there are solids present. Another probe is the simple seven-around-one bundled fiber optic immersion probe available from Visionex, Inc. (Warner Robins, Ga.), specifically the #E2MS-05-785-R probe, which may be preferred in some circumstances because it may have better sensitivity. Another supplier of Raman fiber optic probes is Kaiser Optical Systems, Inc., which is similar to the InPhotonics probe in good performance in rejecting back scattering radiation. In general, a suitable Raman fiber optic probe may be constructed by soldering metal coated, fused silica fiber optic cables into a protective metal sheath. This probe design provides a simple, reliable method of optically sampling and remotely monitoring a chemical composition in a harsh physical environment of a manufacturing process. It may be advisable to position optical filters near the sample to remove background-inducing radiation caused by the fused silica core of the fiber optic cable.

Fiber optic probes have been used to provide a means for transmitting radiation towards a sample and collecting the scattered radiation. Such probes may be constructed with combinations of fiber optics, lenses, and/or mirrors. In one construction, two or more fiber optic lines are secured closely together on the sample end. One or more of these fiber optic lines (typically, one) are used to transmit the radiation into the sample, and one or more additional fiber optic lines (typically, more than one) are used to collect and transmit the scattered radiation back to a detector.

Thus, the same Raman probe may emit radiation and then detect the Raman scattered radiation. Radiation such as laser light may come out one part (for example, one fiber optic cable) of the Raman probe and is focused into the sample to be measured. When the radiation contacts the molecules in the sample, it excites those molecules to a virtual state, which is a higher vibration energy level. When that molecule relaxes and comes back to its ground state, it scatters radiation in all directions. Some of the scattered radiation returns to the Raman probe, where it is gathered by another part (for example, other fiber optic cables) of the Raman probe and fed to the detector. Some of the scattered radiation that returns to the Raman probe reflects the molecular vibrations of the different molecules in the sample. The molecule emits a photon at the vibrational energy at which the molecule is vibrating when it was contacted by the radiation. The various molecules and vibrational energies scatter radiation of different energy levels, which have wavelengths, thereby forming a spectrum.

After the scattered radiation has been collected and transmitted, it is separated using a dispersion element. The dispersion element, which is typically included along with focusing and collimating optical elements in a spectrograph, facilitates the separation of various energy levels of the scattered radiation from one another.

Raman spectrometry has previously been used as the basis for an on-line analytical method, as disclosed in U.S. Pat. No. 5,652,653. The present processes, methods and apparatus differ from the disclosure of that patent at least in that the present processes and apparatus do not employ simultaneously irradiation of a reference material.

The present processes, methods and apparatus are particularly desirable for in situ monitoring of a process for preparing hexene from ethylene, such as by trimerization of ethylene.

In the present methods, both liquid phase and gas phase concentrations may be determined by Raman analysis, while this was not readily done by other techniques. Generally, separate Raman probes will be position in the gas phase and the ligand phase. The use of results of liquid phase and gas phase analyses may provide faster and more accurate results than from current gas chromatographic analyses of flash gas.

Alternatively, monitoring of the process may be accomplished by conducting Raman spectrometric at several points or times before, during and/or after the oligomerization process, thereby providing a method of monitoring the oligomerization reaction as it proceeds. For example, one might measure the concentrations of monomer, hydrogen, and/or other reactants or diluents when they first go into a reactor, when the reaction is underway, and when an effluent is removed from the reactor.

As another alternative, the present processes and methods may be used to control two or more reactors in series. For example, the process of preparing hexene may be performed by connecting a plurality of reactors in series. When reactors are connected in series, the effluent from an upstream reactor may be provided as input to a downstream reactor. A monitoring step may then comprise determining a concentration of monomer in the effluent by Raman spectrometry equipment, and the adjusting step may comprise providing an amount of monomer or comonomer in addition to the effluent to the downstream reactor. This is because it may be desirable to supply an additional amount of monomer or other chemical component to the second, third or later reactors. The additional amount may be determined by references to the concentration of monomer and product in the prior reactor effluent, which may be determined by rapid analysis of the effluent using Raman spectrometry. By adjusting the input to a reactor (usually, how much ethylene monomer is added to the input), hexene may be prepared more selectively, efficiently and economically. Even a two to four percent increase in yield provides a substantial advantage that may be obtained in this way. In preferred embodiments, Raman spectrometric equipment is used to determine concentrations of ethylene and hexene in the influent or effluent of a reactor in series every 2 to 5 minutes, preferably every 30 seconds. This is in contrast to gas chromatographic analysis, which may require up to 40 or 45 minutes for the analysis to be completed.

Trimerization, as used in this disclosure, is defined as the combination of any two, three, or more olefins, wherein the number of olefin, i.e., carbon-carbon double bonds is reduced by two. Reactants applicable for use in a trimerization process are olefinic compounds which can self-react to give useful products such as, for example, the self reaction of ethylene can give 1-hexene and the self-reaction of 1,3-butadiene can give 1,5-cyclooctadiene; and/or olefinic compounds which can react with other olefinic compounds, in other words, co-trimerize, to give useful products such as, for example, co-trimerization of ethylene plus hexene can give 1-decene and/or 1-tetradecene, co-trimerization of ethylene and 1-butene can give 1-octene, co-trimerization of 1-decene and ethylene can give 1-tetradecene and/or 1-docosene. For example, the number of olefin bonds in the combination of three ethylene units is reduced by two, to one olefin bond, in 1-hexene. In another example, the number of olefin bonds in the combination of two 1,3-butadiene units, is reduced by two, to two olefin bonds in 1,5-cyclooctadiene. As used herein, the term 'trimerization' is intended to include dimerization of diolefins, as well as 'co-trimerization', both as defined above.

Suitable trimerizable olefin monomers are those compounds having from about 2 to about 30 carbon atoms per molecule and having at least one olefinic double bond, with ethylene being particularly contemplated, although propylene, butene, and other monomers may also be employed in oligomerization and trimerization processes.

Any catalyst systems suitable for trimerization reactions may be used in the present processes for preparation of oligomers and trimers. Catalyst systems comprising a soluble chromium (II) catalytic metal compound with suitable ligands are preferred for processes for making hexane from ethylene. For examples, numerous suitable catalysts are disclosed in the following U.S. patents, each of which is incorporated herein by reference: U.S. Pat. No. 5,331,104, U.S. Pat. No. 5,376,612, U.S. Pat. No. 5,543,375, U.S. Pat. No. 5,689,028, and U.S. Pat. No. 5,859,303. Those patents also disclose additional monomers, reaction conditions, and products that may be used with the present processes, methods and apparatus.

The reaction products, i.e., olefin trimers as defined in this specification, can be prepared by solution reaction, slurry reaction, and/or gas phase reaction techniques using conventional equipment and contacting processes. Solution reaction techniques are presently preferred. Contacting of the monomer or monomers with a catalyst system can be effected by any manner known in the art.

One convenient method is to suspend the catalyst system in an organic medium and to agitate the mixture in a batch reactor to maintain the catalyst system in solution throughout the trimerization process. Other known contacting methods can be also be employed. Reaction temperatures and pressures can be any temperature and pressure which can trimerize the olefin reactants. Generally, reaction temperatures are within a range of about 0 degree(s) to about 250 degree(s) C. Preferably, reaction temperatures within a range of about 60 degree(s) to about 200 degree(s) C., more preferably, within a range of 80 degree(s) to 150 degree(s) C. and most preferably at about 115 degrees C., are employed. Generally, reaction pressures are within a range of about atmospheric to about 2500 psig. Preferably, reaction pressures within a range of about atmospheric to about 1000 psi and most preferably, at about 800 psi are employed.

The oligomer products have established utility in a wide variety of applications, such as, for example, as monomers for use in the preparation of homopolymers, copolymers, and/or terpolymers.

The olefin oligomerization reaction, or one or more its components or conditions, may be monitored. The monitoring equipment includes a Raman probe which is typically disposed mostly or entirely within the oligomerization reactor. The Raman probe provides an output signal which is representative of the Raman spectrum of the chemical components in reactor or some portion of those components. The output signal from Raman probe is provided to an analyzer which in turn provides a signal to computer. In the computer, the Raman spectrum is monitored, and the oligomerization process may be controlled manually or automatically in response to the spectrum. For example, the computer may send a signal to one or more controllers to adjust the amounts of reactants or diluent added to the reactor or the amount of material. Alternatively, the computer may send a signal to one or more of a stirrer in the reactor withdrawn or a pressure or temperature control for the reactor.

The Raman spectrum may be used to determine the concentrations of the chemical components in the reactor, and/or before or after the reactor. The Raman spectrum may be used to determine the concentration of reactants such as ethylene monomer and hydrogen, products such as hexene or other trimers, and/or diluents such as isobutane.

The peaks of the Raman spectra, or some number that represents such peaks, should be correlated to known concentrations of components through a calibration model before Raman spectrometry is used to determine unknown concentrations. One method of obtaining numerical representation of a peak of the Raman spectrum is by integrating the area of the peak to obtain a single number that represents that peak. One may use a wavelength that is characteristic of a certain component and integrate the area of the peaks at that wavelength to arrive at a number representative for that component. The peaks, or area of the peaks, or some other number representative of certain parts of the Raman spectrum, must then be correlated to a known concentration using a calibration model, which may be based on assigning an area under a certain peak to a known concentration.

In a general procedure for developing a suitable calibration model, a Raman spectrum is obtained for a sample of known concentration of one component, or more preferably a mixture of components, that will be the subject of analysis in the olefin oligomerization process. A plurality of separate regions of the spectrum are selected, based on the known Raman spectra of the components. For example, there is a peak at a wavenumber of about 1620 $cm^{-1}$ that is characteristic of ethylene, so where ethylene will be one of the chemical components of interest, the region of the spectrum at a wavenumber of 1620 $cm^{-1}$ would likely be selected. Next, the areas of the selected regions are determined. A correlation is then identified between the area of the selected region and the concentration of the component(s). By repeating this procedure for different concentrations and different components, and preferably by obtaining multiple spectra and making multiple calculations for each concentration and component, a calibration model may be obtained for the chemical components to be analyzed and monitored. A procedure for the development of a means within a computer for identifying substances using Raman spectroscopy is disclosed in U.S. Pat. No. 4,620,284.

Certain peaks may be known to correspond to a particular component, such as either the product or the monomer. However, other peaks may correspond to more than one component or may be indistinguishable from each other although they correspond to different components. In such cases, obtaining a calibration model that can distinguish and correct quantify these components may seem impossible. It has been observed that such a calibration model is obtainable, though with more difficulty than where the components have peaks that are separate and readily distinguishable. Furthermore, it has been discovered that such a calibration model may be obtained and used even with low resolution Raman spectrometry equipment.

A calibration model may be created using commercially available software, such as the GRAMS/32 and PLSplus/IQ programs available from Galactic Industries Corporation (Salem, N.H.). The calibration model is developed by measuring a sample using the Raman spectrometry equipment, and obtaining a Raman spectrum. The spectrum, or the integrated area or intensity of the peaks of that spectrum, are related to some value, preferably the concentration of monomer or mixture of or chemical components as measured by a gas chromatograph. For example, a Hewlett Packard 6890 with a flame ionization detector may be employed, with a capillary column that is a 60 meter DB1, 0.32 ID, column with a 1 micrometer film thickness. The gas chromatograph may be programmed to start at 40° C., hold for ten minutes, and then increase temperature 12° C. per minute until it reached 275° C. The analysis time for each sample should be approximately forty to forty-five minutes.

The concentrations determined by another analysis or by using a specially made sample having a known concentration are correlated to the Raman spectrum or parts of the spectrum and used to develop a calibration model which can then be used to predict unknowns. The calibration model may be calculated and unknown samples may be analyzed using the Galactic GRAMS/32 program. One may employ additional statistic or computational analysis to confirm or refine the correlation between chemical concentrations and the peaks generated by Raman spectrometric analysis. For example, one may perform partial least squares regression analysis, using the Galactic PLSplus/IQ program. Partial square analysis enables the development of a calibration model where one or more components may have some peaks that overlap.

The correlation predict the concentrations based on what is known and assign concentrations to the unknowns.

Generally, suitable software must be capable of building models between spectral data and concentrations or other characteristics determined some other method and which have a relationship to the spectral response. Such software is typical and commercially available.

In an example of the development of a calibration model, a Visionex probe was placed in the effluent stream of the existing GC reactor take-off line from a trimerization reactor in which ethylene was selectively catalyzed to form 1-hexene. The reactor effluent had a pressure of 450 psig and a temperature of 24° C. Reactor calibration runs were made to build the calibration matrix for the Galactic program for the concentrations of ethylene, hexene, and decene. The spectra from the Raman Systems R-2001 unit showed the peaks that were unique to each component. Ethylene has the —$CH_2$-deformation at 1339 $cm^{-1}$ and the carbon-carbon double bond stretching vibration at 1619 $cm^{-1}$. The product 1-hexene has a double bond stretch at 1640 $cm^{-1}$ and unique peaks at 634 and 908 $cm^{-1}$, which are not present in the solvent or in ethylene. The solvent had major Raman spectral bands at 793, 1021, 1260 and 1462 $cm^{-1}$.

Raman spectra were started at the same time as the GC sampled the reaction effluent. A single spectrum was obtained with an integration time of 30 seconds and a boxcar apodization of 3. The area percent data from the GC unit for each constituent and the Raman spectra from the R-2000 or R-2001 unit were entered into the PLS type 1 algorithm provided by Galactic Industries, GRAMS/32, Version 5.2 program. By use of this calibration model, it was possible to make predictions on the reactant and product concentrations in about 30 seconds.

The PLS-1 calibration file had the following parameters: Calibration Type: PLS-1, Diagnostic: Cross Validation, # Regions: 3, # Samples: 45, # Points: 503, Maximum # Factors: 22, # Files Out: 1, Preprocessing: Mean Centering with Auto Baseline. No samples were excluded and no constituents were excluded. The three spectral regions were 1700-1574, 1550-725, 689-250 $cm^{-1}$. The recommended number of factors was 6. The actual versus predicted values for ethylene had an $R^2$=0.996 for the range 0 to 12 weight %. The actual versus predicted values for hexene had an $R^2$=0.998 for the range 0 to 24 weight %. The actual versus predicted values for solvent had an $R^2$=0.998 for the range 60 to 98 weight %. And, the actual versus predicted values for decene had an $R^2$=0.982 for the range 0 to 1.8 weight %

Ten different reactor samples having associated GC data were analyzed by the Raman spectrometry and a suitable calibration model. In comparison to the GC data, it was possible to predict the levels of 1-hexene within 10% error, ethylene within 15% error, and decene within 10% error, all of these being acceptable error ranges, with the calibration model developed. With this level of accuracy, it is possible to effectively monitor the catalyst activity in the trimerization reaction about 80 times faster than the GC method.

As a second example, an InPhotonics RP-785-01-05-SMA probe was installed in the 1-hexene trimerization reactor, where the pressure and temperature were 800 psig and 115° C., respectively. The InPhotonics probe may be preferable due to the greater safety provided by the brazed sapphire window and stainless steel tubing construction. The calibration model for this on-line monitoring apparatus was built by pumping ethylene, 1-hexene, solvent and decene through the reactor at reaction conditions. The calibration model was then constructed by use of the Grams/32 PLS-1 algorithm, the gas chromatographic data and the Raman spectral data obtained by means of the Raman Systems R-2001C spectrometer.

The Grams/32 PLS-1 calibration file had the following parameters: Calibration Type: PLS-1, Diagnostic: Cross Validation, # Regions: 1 (1700-150 $cm^{-1}$), # Samples: 120, # Points: 1134, Maximum # Factors: 25, # Files Out: 1, Preprocessing: Mean Centering with Auto Baseline. No samples were excluded and no constituents were excluded. The recommended number of factors was 7. The actual versus predicted values for ethylene had an $R^2$=0.990 for the range 0 to 20 weight %. The actual versus predicted values for hexene had an $R^2$=0.998 for the range 0 to 35 weight %. The actual versus predicted values for solvent had an $R^2$=0.996 for the range 49 to 98 weight %. And, the actual versus predicted values for decene had an $R^2$=0.936 for the range 0 to 4.5 weight %.

Additionally, the present processes and apparatus may be automated through the use of the computer, microprocessor, programmably logic controller or other suitable device to automatically adjust one or more conditions in response to the output signal from the Raman probe and/or the Raman analyzer.

Vibrations, movements, and shifting of the various Raman spectrometry equipment can cause unexpected changes in the observed spectra. The types of errors induced are difficult to predict and may cause inaccuracies that result in limited precision. It is desirable to eliminate or minimize the effects of vibrations, movements, and shifting in the Raman spectrometry equipment.

Sample probes may be placed at any location before, during and/or after the olefin oligomerization process, but it is generally advisable to place the Raman probe where it will provide information that is useful for controlling the process and for providing analytical information for calibration purposes. One preferable Raman probe location in a hexene polyolefin production process is near the point in the process where the reaction is near completion. This provides analytical information regarding extent of reaction through the concentration of unreacted monomer or reaction products. Such information allows for improved control of the oligomerization process.

Since the most oligomerization processes are homogeneous, the Raman probe may be placed in the reactor without suffering from the loss of scattered radiation caused by solid particles. Alternatively, the Raman probe may be placed in a product take-off line. In processes for preparing 1-hexene from ethylene, the reaction mixture is a clear liquid. The clear liquid may contain diluent such as cyclohexane and reactant such as ethylene and product such as 1-hexene. The Raman probe may be pointed into the clear liquid or may monitor a gas phase in the head space of a reactor.

The ability to use low resolution Raman spectrometric systems is surprising, in that such systems are typically not capable of resolving certain ethylene peaks from certain hexene peaks. However, by the way the band shapes change, base line resolution is not required, and modeling software and partial least square analysis can be used to detect concentrations without resolving individual peaks. In other words, it is not necessary to resolve the peaks corresponding to ethylene and hexene in the present processes, methods and apparatus. The ability to use a low resolution Raman spectrometer makes the present methods more economical. High cost, high resolution Raman spectrometric equipment generally have a resolution of one to two wavenumbers and can resolve peaks that are only one or two wavenumbers apart. However, it has been discovered that such high resolution is not required for the present processes. A low resolution Raman spectrometer having lower cost may be used. Its resolution may be from about 15 wavenumbers to about 30 wavenumbers. As a result, the low resolution Raman spectrometric equipment cannot resolve certain peaks as clearly as the high resolution spectrometer, but it has been discovered that it is not necessary to have one to two wavenumber resolution for monitoring concentration of components in an oligomerization process.

While the invention has been described in connection with one or more embodiments, it will be understood that the invention is not limited to those embodiments. On the contrary, the invention includes all alternatives, modifications, and equivalents as may be included within the scope of the claims.

What is claimed is:

1. A method for monitoring and controlling an oligomerization process comprising:
    contacting a reaction mixture comprising monomer and a catalyst system in an oligomerization reaction zone;
    forming an oligomer;
    making a first measurement of a concentration of the monomer using Raman spectrometry equipment without simultaneously performing a reference measurement of a reference material with the Raman spectrometry equipment; and
    adjusting an oligomerization reaction condition in response to the first measurement.

2. The method of claim 1, wherein the first measurement is obtained before or within the oligomerization reaction zone.

3. The method of claim 2, comprising:
    making a second measurement of a concentration of the monomer using the Raman spectrometry equipment;
    comparing the first measurement with the second measurement; and
    adjusting the oligomerization reaction condition in response to comparing the first measurement with the second measurement.

4. The method of claim 3, wherein the second measurement is obtained within or after the oligomerization reaction zone.

5. The method of claim 1, wherein the first measurement is obtained from the oligomerization reaction zone in a gas phase or a liquid phase, or a combination thereof.

6. The method of claim 1, wherein the making the first measurement comprises:
    obtaining a Raman spectrum of the reaction mixture, and determining the first measurement through the use of a calibration model.

7. The method of claim 6 comprising developing the calibration model using partial least squares analysis.

8. The method of claim 1, wherein the Raman spectrometry equipment is low resolution Raman spectrometry equipment.

9. The method of claim 8, wherein the low resolution Raman spectrometry equipment has a resolution of about 15 wavenumbers to about 30 wavenumbers.

10. The method of claim 1, wherein the reaction mixture comprises hydrogen.

11. The method of claim 1, wherein forming the oligomer comprises a trimerization reaction.

12. The method of claim 1, wherein the monomer comprises ethylene and the oligomer comprises 1-hexene.

13. The method of claim 1, wherein:
    the oligomerization reaction zone comprises two or more reactors in series;
    effluent from an upstream reactor is provided as input to a downstream reactor;
    making the first measurement comprises determining a concentration of the monomer in the effluent by the Raman spectrometry equipment; and
    adjusting an oligomerization reaction condition comprises adjusting an amount of monomer or comonomer fed to the downstream reactor in response to the first measurement.

* * * * *